United States Patent [19]

Colton

[11] 4,070,165
[45] Jan. 24, 1978

[54] PRETREATMENT OF RAW NATURAL GAS PRIOR TO LIQUEFACTION

[75] Inventor: John W. Colton, Des Plaines, Ill.

[73] Assignee: UOP Inc., Des Plaines, Ill.

[21] Appl. No.: 641,119

[22] Filed: Dec. 15, 1975

[51] Int. Cl.$^2$ .................. B01D 53/14; F25J 3/08
[52] U.S. Cl. .................................... 55/30; 55/74;
    55/89; 62/17; 62/18; 62/23
[58] Field of Search .................. 62/17, 18, 20, 23, 27,
    62/28; 55/84, 89, 30, 68, 73, 74, 75, 76, 12

[56] References Cited

U.S. PATENT DOCUMENTS

| | | | |
|---|---|---|---|
| 2,557,171 | 6/1951 | Bodle et al. ............................. | 62/39 |
| 2,744,394 | 5/1956 | Newton .................................. | 62/17 |
| 2,777,305 | 1/1957 | Davison ................................. | 62/17 |
| 2,849,371 | 8/1958 | Gilmore ................................. | 55/89 |
| 2,973,834 | 3/1961 | Cicalese ................................ | 55/89 |
| 3,664,091 | 5/1972 | Hegwer ................................. | 62/17 |

*Primary Examiner*—Hiram H. Bernstein
*Attorney, Agent, or Firm*—James R. Hoatson, Jr.; Robert W. Erickson; William H. Page, II

[57] ABSTRACT

High pressure raw natural gas is prepared for liquefaction by first removing water and acid gases and then expanding the gas from the wellhead pressure to remove shaft horsepower. The expanded gas is scrubbed with a $C_4$ rich liquid previously separated from the gas to remove heavy hydrocarbons and then further dried and passed to the liquefaction zone.

2 Claims, 1 Drawing Figure

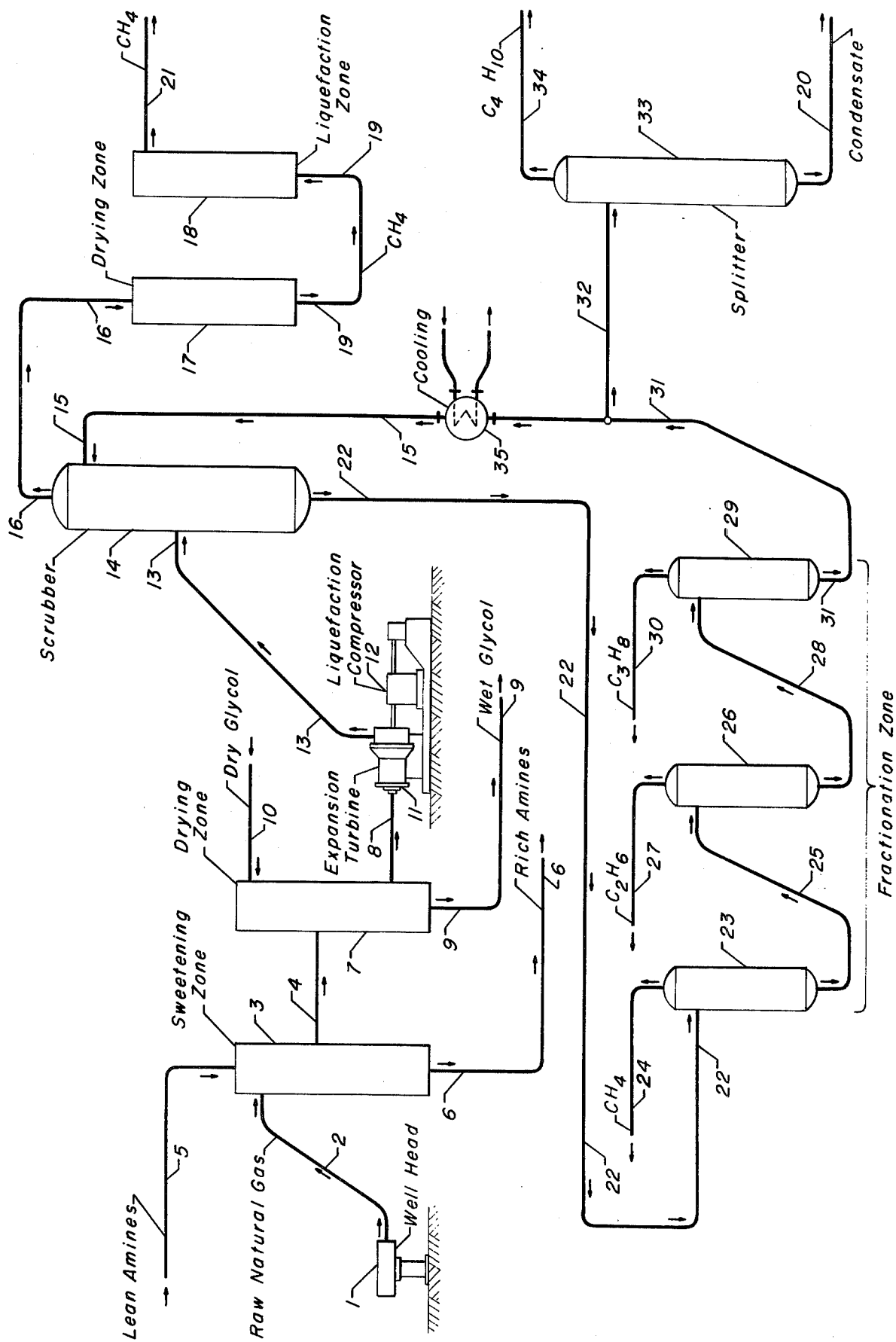

4,070,165

PRETREATMENT OF RAW NATURAL GAS PRIOR TO LIQUEFACTION

FIELD OF THE INVENTION

The invention relates to a separatory process for gaseous hydrocarbons. It more specifically relates to a method of purification and separation for raw natural gas such as is found in Classes 62-12 to 62-41.

PRIOR ART

A large number of commercial processes are in use for treating and separating raw wellhead gas. The individual elements or steps used in the different processes are each well known to those skilled in the art, and most recent advances have been in the area of more efficient designs, combinations or usages of these known components. For instance, U.S. Pat. No. 3,393,527 (Cl. 62-16) presents a method of separating heavier hydrocarbons from a natural gas wherein work is performed through expanding the gas. U.S. Pat. No. 3,653,220 (Cl. 62-22) presents a process for recovering helium in which the raw gas is dried and treated to remove $CO_2$ at high pressure. This process differs from the present invention by the partial decompression and preliminary cooling of the gas prior to its expansion in a power recovery turbine.

A large amount of literature exists as to individual operations for the treatment of natural gas. For instance, the *Engineering Data Book,* 9th Ed., published by the Natural Gas Processers Suppliers Association, Tulsa, Oklahoma gives a description and design estimate basis for many types of gas dehydration techniques including the use of liquids such as glycols, solid desiccants and expansion refrigeration. This same reference also has a section on treating natural gas to remove acid gases by the processes of chemical reaction, physical solution and adsorption. Many commercial processes used for drying, sweetening, recovering natural gas liquids, manufacturing liquefied natural gas and removing carbon dioxide, hydrogen sulfide and nitrogen are described in the section comprising pages 93–122 of the April 1971 edition of *Hydrocarbon Processing.*

SUMMARY OF THE INVENTION

The invention provides a process for pretreating raw wellhead gas which reduces the liquefaction refrigeration power requirements by utilizing the energy recovered in expanding the raw gas and which reduces the volume of gas which must be dried in expensive desiccant bed prior to liquefaction. A broad embodiment of the invention comprises the steps of sweetening and drying the raw natural gas at a pressure above 800 psig., depressuring the gas to a pressure under 200 psig. in an energy recovery means delivering shaft horesepower, scrubbing the resultant depressured gas with a lean hydrocarbon stream to remove hydrocarbons having two or more carbon atoms per molecule, passing the remaining gas stream through a second drying operation to provide a gas stream suitable for liquefaction, stripping $C_1$-$C_3$ hydrocarbons from the rich hydrocarbon stream formed by scrubbing the depressured gas stream and using a portion of the resultant liquid as the lean hydrocarbon stream.

DESCRIPTION OF DRAWING

The drawing illustrates the preferred embodiment of the invention. A stream of raw natural gas is removed from the wellhead 1 and transported through line 2 at a pressure substantially equal to the wellhead pressure. This stream is first passed through a sweetening zone 3 wherein acid gases such as $H_2S$ and $CO_2$ are removed. Preferably, this is performed by countercurrent contacting with a stream of a lean amine solution entering in line 5, and the resultant rich amine solution is removed via line 6. The now sweetened natural gas stream continues through line 4 to a first drying zone 7 wherein water is transferred to the dry glycol entering in line 10 to form a wet glycol stream removed in line 9. The resultant stream of dried natural gas is then passed through line 8, which may be a rather lengthy gathering or transfer line, to an expansion turbine 11. The enthalpy of the gas stream is reduced through expansion and the delivery of shaft horsepower to an energy consuming device such as a compressor 12 in the downstream liquefaction operation.

The depressurized gas is transported into a scrubber 14 through line 13 and contacted with a lean hydrocarbon stream entering in line 15. Conditions maintained within the scrubber effect the transfer of some methane and very substantial percentages of heavier hydrocarbons into the lean hydrocarbon stream to form a rich hydrocarbon stream removed in line 22. This rich stream is then stripped in fractionation column 23 to remove methane in line 24. The remaining hydrocarbons pass via line 25 into column 26, in which a stream of ethane removed in line 27 is separated. Finally, the hydrocarbons enter column 29 through line 28, and a stream of propane is removed via line 30.

This fractionation sequence produces a stream of $C_4$ plus liquid removed in line 31. A net liquid product stream is diverted into line 32 and passed into a splitter column 33, which produces a stream of relatively pure butane discharged through line 34. A stream of naphtha like condensate is removed via line 20. The remaining portion of the $C_4$ plus liquid is cooled in a heat exchange means 35 and passed into the scrubber as the lean hydrocarbon stream.

A methane rich gas stream is removed from the scrubber through line 16 and passed into a second drying zone 17. This is preferably a solid desiccant type of drying operation. The resultant dry gas stream is now suitable for passage into a liquefaction zone 18, from which a liquid stream comprising methane is removed via line 21.

Those skilled in the art will recognize that a great many alternatives are available in the practice of various steps of this process. These are described in detail below. Many accessories and subsystems have not been shown for the purposes of clarity and simplicity. This drawing and description are therefore not intended to limit the scope of the broad embodiment of the invention to the specific arrangement illustrated.

DETAILED DESCRIPTION

Raw natural gas must be treated prior to its liquefaction for several reaons. These include removing compounds which interfere with or hinder the liquefaction process, the recovery of hydrocarbon liquids and meeting the product specifications set for the products. For instance, the gas must be dried to prevent ice formation in the process during cryogenic operations and hydrogen sulfide cannot be tolerated due to its toxic nature. The present invention therefore finds utility in the pretreatment of natural gas to be liquefied.

Raw naturalgas is often produced at a wellhead pressure of from 800 psig. to 4,000 psig. or higher. Very high pressure gas is normally throttled to a pressure of about 1500 psig. at the wellhead to allow the use of more easily fabricated piping, flanges and valves. This gas is then passed into a sweetening zone operated at conditions effective to cause the removal of acid gases including hydrogen sulfide and carbon dioxide. These conditions will include a pressure near the wellhead pressure or the lower pressure of the throttled raw gas. This zone may utilize any system which is capable of removing these gases effectively down to a level of less than 50 ppm. and which is economical at this high pressure. $CO_2$ is normally present to a greater extent in natural gas than $H_2S$. It is removed to prevent it from freezing out in subsequent cryogenic processing.

It is preferred that the sweetening zone comprises an amine treating operation wherein the raw gas is passed through a contactor countercurrently to a liquid amine solution. The amine is used as an aqueous solution and has no selectivity for $H_2S$ or $CO_2$. Ethanolamines are one of the most commonly used reagents and are well suited for gases rich in heavier hydrocarbons. Diethanolamine (DEA) is used when the gas stream contains carbonyl sulfide which reacts irreversibly with monoethanolamine (MEA). This type of sweetening is similar to that performed in the Girbotol process.

In MEA units the total acid gas pickup is normally limited to about 0.33 moles of acid gas/mole of MEA. The concentration of the MEA is generally held within the 15 to 18 wt.% range to limit corrosion. DEA may be used at concentrations of up to 25 wt.%. With both solutions the contactors and the associated amine strippers will typically have from 18 to 22 trays.

Other processes are also available for sweetening and well known to those skilled in the art. For instance, the Sulfinol process uses a solvent composed of sulfolane (tetrahydrothiopene dioxide), di-isopropanolamine (DIPA) and water. Diglycolamine (DGA) at concentrations ranging from 50 to 70 wt.% in an aqueous solution can also be used to sweeten natural gas containing carbonyl sulfide and/or carbon disulfide. DGA is sometimes preferred since it can be used in colder climates than the other amines.

Another grouping of processes are the hot carbonate type developed by the U.S. Bureau of Mines. They employ an aqueous solution of potassium carbonate which is circulated through an absorber and regenerator at a temperature of about 230° to 240° F. The process is limited in that it cannot be used on a gas stream containing only $H_2S$. The most popular hot carbonate processes contain a proprietary activator. These are known as the Benfield process, the Catacarb process and the Giammarco-Vetrocoke process.

Sweetening may also be performed through the use of a process in which the $H_2S$ is reacted with a hydrated iron oxide and the iron oxide is then intermittently regenerated or replaced. This method is mainly used with gases having a low concentration of $H_2S$.

The sweetening zone may contain a separate system for the removal of $H_2S$. One system suitable for this is the Stretford process in which the gas is washed with an aqueous solution containing sodium carbonate, sodium vanadate, anthraquinone disulfonic acid and traces of chelated iron. Only small amounts of $CO_2$ may be removed by this process, but essentially complete removal of $H_2S$ is possible. The process may be operated over a wide pressure range starting at a few inches of mercury and is normally run at a temperature of from ambient to 120° F. The hydrogen sulfide dissolves in the alkaline solution and is oxidized to elemental sulfur by reaction with the vanadate. The circulating liquid is regenerated by air blowing, and the sulfur forms a scum removed by froth flotation.

Physical solvent processes also find application in sweetening. The more popular processes use such solvents an anhydrous propylene carbonate, a dimethylether of polyethylene glycol and methanol. The absorber is a conventional trayed or packed tower. Regeneration is by one or more of the following techniques: multi-stage flashing, low temperature stripping with an inert gas, or heating and stripping with the liquid vapor.

Those skilled in the art will appreciate the fact that this has not been an exhaustive description of the processes which may be used in the sweetening zone. For instance, sulfur compounds can also be removed through the use of adsorption techniques including molecular sieve processes. Further details of these processes may be obtained from the references previously cited.

The now sweetened natural gas, while at a pressure which is reduced from that at the wellhead only by the inherent pressure drops within the transfer lines and sweetening zone and any throttling, is then passed into a first drying zone which is also operated at this high pressure. Water is removed at this point to prevent the formation of hydrates in transmission lines and to meet water dew point requirements. The basic dehydration techniques include absorption using solid or liquid desiccants and dehydration be expansion refrigeration. This may include intentionally freezing out the water. In general any system capable of drying the gas down to about a −20° F. dew point may be used. However, it is preferred that the first drying zone effects the formation of a stream of dried natural gas having a dew point of −40° F. (about nine pounds water per million SCF). A nominal −40° F. dew point gas will have dry pipeline walls at 900 psig. pressure and any temperature above 38° F. The degree of water removal necessary in the first drying zone will depend on several factors including the ambient temperature to which the transmission lines are exposed. Thus, in artic climates the nominal dew point (measured at 14.7 psia.) will have to be much lower than −20° F.

It is preferred that the first drying zone consists of a glycol type drying system. The most commonly used glycols are triethylene glycol (TEG), diethylene glycol (DEG), and ethylene glycol (MEG). The basic elements to a glycol drying system are an inlet gas scrubber, a glycol gas contactor, a glycol regenerator and a heat-exchanger. The drying process comprises pumping regenerated glycol to the top tray of a contactor (absorber) and removing water-rich glycol from the bottom of the contactor. This glycol is heat exchanged with regenerated glycol and passed into the regenerator. The regenerator may be operated at atmospheric pressure within a temperature range of about 375° to 400° F. This mode of operation can produce regenerated TEG having a concentration of 99.0 wt.%. A stripping gas at rates up to 14 scf/gallon TEG is used in the regenerator if higher glycol concentrations are desired. Glycol circulation rates may vary from about 2 to 5 gallons of glycol per pound of water to be removed. The countercurrent contacting may be carried out over a range of temperatures, with operation at the minimum available cooling water temperatures below 120° F. being preferred. The recirculation rate and the number of trays used in the contactor will vary depending on such factors as the desired dew point depression. Typical contactors have from four to eight or more trays.

Solid-desiccant dehydration operations normally use a material which is regenerated in two or more beds used on a swing basis. It is possible to reduce the water content of the gas to less than 1 ppm. with a solid desiccant. As a result they are commonly used to dry gas prior to cryogenic processing and are preferred for use in the second drying zone of the subject invention. The specific desiccant to be used depends on the composition of the gas stream and the dew point required. Some desiccants are adversely affected by acid gases, well treating chemicals and heavier hydrocarbons. Activated alumina, silica gel and silica-alumina beads are some of the more common suitable materials. Molecular sieves, such as a type 4A sieve, are another group of suitable materials. Further details on the use of desiccants can be obtained from standard references including for instance U.S. Pat. No. 3,205,683.

Dehydration can also be performed through expansion refrigeration. This method is not preferred since it lowers the pressure of the gas stream. However, it may be utilized when the available field pressure is extremely high. Often a hydrate inhibitor is injected either continuously or intermittently. Ethylene glycol is the most commonly used, with other inhibitors being diethylene glycol and methanol. The glycol and its absorbed water are separated from the gas stream along with liquid hydrocarbons. U.S. Pat. No. 2,537,270 illustrates a natural gas dehydration process using expansion and is representative of the level of the art.

The terms "sweetening" and "drying zone" are intended to refer to all functional means for performing these operations. It is consistent with this that the zones may be combined. Therefore the removal of both acid gases and water in a single integrated system is intended as within the scope of the invention. Some solvent and molecular sieve operations are capable of removing both $H_2S$ and water from the gas. For instance, U.S. Pat. No. 3,837,143 (Cl. 55-32) describes the use of a dialkyl ether of a polyalkylene glycol ether containing 2 to 15 wt.% water as solvent, and U.S. Pat. No. 3,841,058 (Cl. 55-33) presents an improvement in the removal of water and carbon dioxide by solid absorbents and the regeneration of the absorbents. There may also be included within or in conjunction with the sweetening and drying zones a means for removing nitrogen and thereby increasing the heating value of the gas. U.S. Pat. No. 3,791,157 illustrates one such nitrogen removal process.

Following the removal of acid gases and water, the remaining portion of the natural gas stream is passed into an energy recovery means in which the gas stream is depressured. The energy recovery means may be located a substantial distance away from the first drying zone. This is because economics generally favor transportation of gases at an elevated pressure. The energy recovery means may be of any type which will deliver shaft horsepower and effect a reduction in the enthalpy of the gas stream. Energy can be effectively recovered down to a pressure of about 100 to 300 psig. Consideration must of course be given to the pressure desired for the subsequent scrubbing and liquefaction operations. It is preferred that the energy recovery means drive equipment used in the liquefaction zone. It is also preferred that the energy recovery means is a turboexpander. These devices are already in widespread use and their design is well known to those skilled in the art. More specific information is available from standard references including the article on pages 227-234 of February 1973 edition of the *Journal of Engineering for Industry*.

The resultant low pressure stream of dried and sweetened natural gas is then passed into a scrubbing zone in which it is countercurrently contacted with a lean liquid hydrocarbon stream. The purpose of this operation is to remove heavier hydrocarbons, a term which is intended to refer to all hydrocarbons having more than two carbon atoms per molecule. The scrubbing zone should remove over 50% of the ethane and substantially all of the propane, butanes, pentanes, etc. As used in this context the term substantially all is intended to refer to the removal of over 90 mol.% of each hydrocarbon. This results in the formation of a net gas stream rich in methane, but also containing nitrogen and ethane. This net gas stream is the charge stock for the liquefaction zone and should contain at least 80% methane. The volume of the net gas stream will normally be about 80 to 85% of the raw natural gas. This is advantageous as it allows a reduction in the required size of the downstream second drying zone.

The design and operation of scrubbing zones is well known. It is preferred that a vertical column containing five or more trays is utilized, but a packed tower may be substituted. Higher pressures favor the transfer of the heavier hydrocarbons into the scrubbing liquid, and it is therefor preferred that the scrubbing zone is operated at a pressure above 50 psig. A temperature of from about 60° F. to 200° F. should be maintained in the zone. As the scrubbing operation is exothermic, this may require the subcooling of one of the feed streams or the provision of intermediate cooling means. It is preferred that $C_4$ to $C_6$ hydrocarbons predominate in the scrubbing liquid and that hydrocarbons having more than 6 carbon atoms per molecule comprise less than 30% of the circulating mixture. A circulation rate of about 1 to 3 moles of liquid per mole of incoming gas is normally utilized.

The scrubbing liquid is removed from the scrubbing zone as a resultant rich liquid hydrocarbon stream and passed into a fractionation zone. This zone may take one of several forms depending on the desired products. It is preferred that the fractionation zone comprises three columns, each of which produces a relatively pure stream of methane, ethane and propane respectively. The methane stream from this zone may be admixed with the net gas stream of the scrubbing zone. Alternatively, all three of these gases may be removed as a single stream, and this steam if desired can be further fractionated. The conditions used within the zone will of cource vary with its configuration and may be determined by those skilled in the art. For instance, a rather complex method of fractionating natural gas components to remove heavy hydrocarbons is illustrated in U.S. Pat. No. 3,393,527.

In the subject process a portion of the resultant $C_4$-plus lean liquid equal to the amount of its component materials picked up in the scrubbing zone is divided off. This amount is preferably split in another fractionating column to yield a stream of butanes and a stream of liquefied condensate. The remaining portion of the fractionation zone effluent is then cooled and passed into the scrubbing zone as a lean liquid hydrocarbon stream used as the scrubbing liquid.

The methane-rich net gas stream formed in the scrubbing zone is passed into a second drying zone. The nature of this zone may vary, but it must be capable of drying the gas down to a dew point of roughly −240° F. or below. Preferably, the dry gas stream produced in the second drying zone will have a dew point of −260° F. A solid desiccant system such as previously described is therefore preferred, and especially preferred for use are alumina and molecular sieves.

In accordance with the preceding description, the preferred embodiment of my invention may be characterized as a process for the treatment of raw natural gas prior to liquefaction which comprises: passing a stream of raw natural gas having a pressure above 800 psig. through a sweetening zone operated at conditions effective to remove carbon dioxide and hydrogen sulfide therefrom and to thereby effect the formation of a stream of sweetened natural gas; passing the stream of sweetened natural gas through a first drying zone operated at conditions effective to remove water therefrom and to effect the formation of a stream of dried natural gas having a dew point below −20° F.; depressurizing the stream of dried natural gas in an energy recovery means developing shaft horsepower to a pressure under 300 psig.; contacting the stream of dried natural gas with a lean liquid hydrocarbon stream in a scrubbing zone operated at conditions effective to cause the transfer of substantially all hydrocarbons having more than two carbon atoms per molecule into the lean liquid hydrocarbon stream and to effect thereby the formation of a methane-rich gas stream and a rich liquid hydrocarbon stream; passing the methanerich gas stream into a second drying zone operated at conditions effective to remove water from the methane-rich gas stream and to effect the formation of a dry gas stream having a dew point below about 31 240° F. and suitable for passage into a liquefaction zone; passing the rich liquid hydrocarbon stream into a fractionation zone operated at conditions effective to remove hydrocarbons having from one to three carbon atoms per molecule from the rich liquid hydrocarbon stream and to effect thereby the formation of a $C_4$-plus liquid hydrocarbon stream; and dividing the $C_4$-plus liquid hydrocarbon stream into two portions and passing one of the portions into the scrubbing zone as the lean liquid hydrocarbon stream.

The dry gas stream produced in the second drying zone will normally be suitable for insertion directly into a liquefaction zone. Presently three basic cycles for the liquefaction of natural gas are known to those skilled in the art. These are generally referred to as the Cascade Cycle, the Multi-Component Refrigerant Cycle and the Expander Cycle. Each is described in some detail in U.S. Pat. No. 3,724,226 (Cl. 62–39). These processes are each subject to much variation. Further examples and details of liquefaction methods may be obtained by referring to U.S. Pat. No. 3,254,495; 3,315,477 and 3,763,658.

I claim as my invention:

1. A process for the treatment of raw natural gas prior to liquefaction which comprises:
    a. passing a stream of raw natural gas having a pressure above 800 psig. through a sweetening zone operated at conditions effective to remove carbon dioxide and hydrogen sulfide therefrom and to thereby effect the formation of a stream of sweetened natural gas;
    b. passing the stream of sweetened natural gas through a first drying zone operated at conditions effective to remove water therefrom and to effect the formation of a stream of dried natural gas having a dew point below −20° F.;
    c. depressurizing the total stream of dried natural gas in an energy recovery means developing shaft horsepower to a pressure under 300 psig.;
    d. contacting said total stream of dried natrual gas possessing a pressure of less than 300 psig. with a lean liquid hydrocarbon stream in a scrubbing zone operated at conditions effective to cause the transfer of substantially all hydrocarbons having more than two carbon atoms per molecule into the lean liquid hydrocarbon stream and to effect thereby the formation of a methane-rich gas stream and a rich liquid hydrocarbon stream;
    e. passing the methane-rich gas stream into a solid desiccant drying zone operated at conditions effective to remove water from the methane-rich gas stream and to effect the formation of a dry gas stream having a dew point below about −240° F.;
    f. passing the rich liquid hydrocarbon stream into a fractionation zone operated at conditions effective to separate streams rich in methane, ethane and propane respectively from the rich liquid hydrocarbon stream and to effect thereby the formation of a $C_4$-plus liquid hydrocarbon stream; and,
    g. dividing the $C_4$-plus liquid hydrocarbon stream into two portions and passing one of the portions into the scrubbing zone as the lean liquid hydrocarbon stream.

2. The process of claim 1 further characterized in that the first drying zone utilizes a glycol solution as a drying media and in that an amine solution is utilized in the sweetening zone.

* * * * *